US010335223B2

(12) United States Patent
Neugebauer et al.

(10) Patent No.: US 10,335,223 B2
(45) Date of Patent: Jul. 2, 2019

(54) HEMOSTASIS INSTRUMENT

(75) Inventors: Alexander Neugebauer, Moessingen (DE); Klaus Fischer, Nagold (DE); Markus D. Enderle, Tuebingen (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 0 days.

(21) Appl. No.: 13/881,269

(22) PCT Filed: Oct. 24, 2011

(86) PCT No.: PCT/EP2011/068542

§ 371 (c)(1), (2), (4) Date: Apr. 24, 2013

(87) PCT Pub. No.: WO2012/055816

PCT Pub. Date: May 3, 2012

(65) Prior Publication Data

US 2013/0218069 A1 Aug. 22, 2013

(30) Foreign Application Priority Data

Oct. 26, 2010 (DE) ........................ 10 2010 060 163
Oct. 26, 2010 (DE) ........................ 10 2010 060 165

(Continued)

(51) Int. Cl.
*A61B 18/08* (2006.01)
*A61B 18/04* (2006.01)

(Continued)

(52) U.S. Cl.
CPC ............ *A61B 18/08* (2013.01); *A61B 5/4836* (2013.01); *A61B 18/042* (2013.01); *A61M 5/00* (2013.01);

(Continued)

(58) Field of Classification Search
CPC .................. A61B 18/042; A61B 18/08; A61B 2018/00589

(Continued)

(56) References Cited

U.S. PATENT DOCUMENTS 4,781,175 A * 11/1988 McGreevy et al. ............ 606/40
5,449,356 A 9/1995 Walbrink et al.

(Continued)

FOREIGN PATENT DOCUMENTS

DE 3642077 6/1988
DE 19537897 3/1997

(Continued)

OTHER PUBLICATIONS

International Search Report for PCT/EP2011/068542, English Translation attached to original, Both completed by the European Patent Office dated Jan. 25, 2012, All together 7 Pages.

(Continued)

*Primary Examiner* — Linda C Dvorak
*Assistant Examiner* — Bo Ouyang
(74) *Attorney, Agent, or Firm* — Brooks Kushman P.C.

(57) ABSTRACT

A hemostasis instrument for actively stopping the bleeding, in particular after an open, laparoscopic, or endoscopic operation on a patient, having several hemostasis components. The hemostasis instrument has at least the following hemostasis components: a thermal hemostasis device for tissue coagulation by producing a temperature above the coagulation temperature of biological tissue by means of a coagulation electrode; a biochemical hemostasis device for producing a silent electric discharge by means of at least one discharge electrode, and an insulating device, wherein the insulating device is arranged between the discharge electrode and the tissue to be treated; a supplying device for supplying substances that influence blood clotting to the (Continued)

1 7 15 3 17 19 9 21 23 tissue to be treated; and a supply device for supplying noble gas to the tissue to be treated.

20 Claims, 4 Drawing Sheets

(30) Foreign Application Priority Data

Dec. 7, 2010 (DE) ........................ 10 2010 061 058
Dec. 7, 2010 (DE) ........................ 10 2010 061 059

(51) Int. Cl.
*H05H 1/24* (2006.01)
*A61B 5/00* (2006.01)
*A61M 5/00* (2006.01)
*A61B 18/14* (2006.01)
*A61B 18/00* (2006.01)

(52) U.S. Cl.
CPC ....... *H05H 1/2406* (2013.01); *A61B 18/1477* (2013.01); *A61B 2018/0063* (2013.01); *A61B 2018/00559* (2013.01); *A61B 2018/00589* (2013.01); *A61B 2018/00994* (2013.01); *A61B 2018/147* (2013.01); *A61B 2018/1425* (2013.01); *H05H 2245/122* (2013.01)

(58) Field of Classification Search
USPC ......................................... 606/27, 28, 40, 49
See application file for complete search history.

(56) References Cited

U.S. PATENT DOCUMENTS

| | | | | |
|---|---|---|---|---|
| 5,707,402 | A | 1/1998 | Heim | |
| 5,759,179 | A * | 6/1998 | Balbierz | A61M 25/0606 604/164.01 |
| 5,769,826 | A * | 6/1998 | Johnson | A61M 5/3232 600/576 |
| 6,210,402 | B1 * | 4/2001 | Olsen et al. | 606/32 |
| 6,391,027 | B1 * | 5/2002 | Farin et al. | 606/45 |
| 7,182,762 | B2 | 2/2007 | Bortkiewicz | |
| 7,291,145 | B2 | 11/2007 | Seid | |
| 7,517,347 | B2 * | 4/2009 | Hug | A61B 18/042 604/113 |
| 8,057,446 | B2 | 11/2011 | Kane et al. | |
| 8,725,248 | B2 | 5/2014 | Gutsol et al. | |
| 2005/0143726 | A1 | 6/2005 | Bortkiewicz | |
| 2006/0084158 | A1 | 4/2006 | Viol | |
| 2008/0125742 | A1 * | 5/2008 | Podhajsky | 604/500 |
| 2008/0269590 | A1 | 10/2008 | Wedel | |
| 2008/0275409 | A1 | 11/2008 | Kane et al. | |
| 2009/0024122 | A1 | 1/2009 | Fischer | |
| 2009/0076505 | A1 * | 3/2009 | Arts | A61B 18/042 606/49 |
| 2009/0206062 | A1 | 8/2009 | Kuo | |
| 2010/0114092 | A1 | 5/2010 | Eisele et al. | |
| 2010/0125267 | A1 * | 5/2010 | Lee et al. | 606/27 |
| 2010/0324449 | A1 * | 12/2010 | Rostaing | A61B 5/1411 600/573 |
| 2011/0319887 | A1 * | 12/2011 | Keppel | 606/41 |
| 2012/0303016 | A1 | 11/2012 | Fischer et al. | |

FOREIGN PATENT DOCUMENTS

| | | |
|---|---|---|
| DE | 10328181 | 8/2004 |
| DE | 102004009978 | 4/2005 |
| DE | 102005021304 | 11/2006 |
| DE | 19858375 | 7/2008 |
| DE | 102007003836 | 8/2008 |
| DE | 102007019333 | 11/2008 |
| DE | 102009002278 | 10/2010 |
| DE | 102010015899 | 8/2011 |
| EP | 0872211 | 7/2000 |
| JP | H06178780 | 6/1994 |
| JP | 2002301088 | 10/2002 |
| JP | 2002301088 A | 10/2002 |
| JP | 2006527613 | 12/2006 |
| JP | 2007516788 | 6/2007 |
| JP | 2008539007 | 11/2008 |
| JP | 2008543355 | 12/2008 |
| JP | 2010525873 | 7/2010 |
| JP | 2010525873 A | 7/2010 |
| JP | 2013518634 | 5/2013 |
| WO | 2006116252 | 11/2006 |
| WO | 2010009103 | 1/2010 |
| WO | 2005065560 A1 | 7/2015 |

OTHER PUBLICATIONS

Office Action for DE 10 2010 061 058.5, dated Sep. 30, 2011, 6 Pages together with Machine Translation.
Office Action for DE 10 2010 061 059.3, dated Oct. 20, 2011, 10 pages together with Machine Translation.
Japanese Office Action for Japanese Application No. 2013-535388, dated Jun. 24, 2014, 3 Pages, together with English Translation.
Chinese Office Action for Chinese Application No. 201180051550.0, dated Dec. 3, 2014, 10 pages.
Chinese Office Action for Chinese Patent Application No. 201180051550.0, dated Jul. 27, 2015, 9 pages. (No translation available).
Japanese Office Action for Japanese Patent Application No. 2013-535388, dated Apr. 28, 2015, 3 pages. (No translation available).
Kalghatgi, Sameer U., “Mechanism of Blood Coagulation by Nonthermal Atmospheric Pressure Dielectric Barrier Discharge Plasma”, IEEE Transactions on Plasma Science, vol. 35, No. 5, Oct. 2007, pp. 1559-1566.
Korean Office Action for Application No. 10-2013-7011436, dated Apr. 29, 2015 together with English Translation, (8 pages).
Japanese Office Action, JP Patent App. No. 2013-535388; dated Feb. 2, 2016, 3 pages (including English Translation).
European Office Action dated Feb. 13, 2018 corresponding to related EP Application No. 11773008.5 (no English translation).

* cited by examiner

HEMOSTASIS INSTRUMENT

CROSS-REFERENCE TO RELATED APPLICATION

This application is the U.S. national phase of PCT Application No. PCT/EP2011/068542 filed on Oct. 24, 2011, which claims priority to German Patent Application Nos. 102010060163.2 filed on Oct. 26, 2010, 102010060165.9 filed on Oct. 26, 2010, 102010061058.5 filed on Dec. 7, 2010, and 102010061059.3 filed Dec. 7, 2010, the disclosures of which are incorporated in their entirety by reference herein.

The invention relates to a hemostasis instrument in accordance with the preamble of claim 1 and to a surgical apparatus for stopping bleeding in accordance with the preamble of claim 9.

Many surgical operations, in particular open, laparoscopic or endoscopic operations, require bleeding be actively stopped. If bleeding occurs, this must be stopped because otherwise the operation site is quickly covered by blood and an effective continuation of the operation often becomes impossible. Moreover, in the case of heavy bleeding, there is an acute risk of the patient bleeding to death if bleeding is not stopped within a short period of time. In the case of heavy bleeding, banked blood is often required, which, in principle, is a scarce commodity and moreover often rejected by patients for religious or other reasons. Moreover, a certain element of risk of an infection always exists if banked blood is used. Conventional methods and devices for stopping bleeding make use of mechanical, electrosurgical or laser surgical means. Moreover, there is the option of using fibrin adhesives or collagen dressings to stop bleeding. From a mechanical point of view, use can be made of a suture or hemoclip to stop bleeding. Compared to electrosurgical and laser surgical hemostasis, mechanical hemostasis is connected with a significantly greater expenditure of time and more difficult handling. Moreover, there can be suture and hemoclip intolerance, such as intolerance to foreign material, in particular as a result of string material and metallic substances. Hemoclips can wander, open and, in the worst case, perforate organs or incorrectly also "close off" neighboring structures. Sutures can cause adhesions or concretions and abscesses. Particularly in endoscopic, but also laparoscopic, cases not all bleedings are possible as a result of the reachability of bleeding by the mechanical means. Mechanical hemostasis methods are generally not suitable for diffuse bleeding.

All conventional methods of electrosurgery and laser surgery are subsumed by the so-called "thermal hemostasis". Electrosurgical methods include methods from the field of electrosurgery, contact-clamping coagulation and contactless plasma coagulation, such as, for example, argon plasma coagulation, and also low bleeding electrosurgical incision methods. Hemostasis by means of laser and by means of electrosurgery target a heating of bleeding tissue site, wherein the hemostasis is brought about by exogenous heating of the tissue in laser surgery and endogenous heating of the tissue in electrosurgery. A disadvantage here is the occurrence of high local temperatures of up to 300° C. and an accompanying risk of thermal damage to adjacent tissue. Moreover, compared to mechanical damage of the tissue by a scalpel, wounds generated by laser and electrosurgery only heal in a delayed fashion. In many cases, it was possible to show that even thermally induced wounds can cause concretions of organs amongst themselves or concretions with the abdominal wall. These findings are particularly problematic in almost all operations in the field of gynecology, but also in other surgical specialist disciplines. Particularly, many young women are affected by this, since the typical operation indications relate to women of childbearing age (removal of ovarian cysts, removal of a myoma, oviductal surgery). If adhesions occur post surgery, chronic pain states, fertility disorders and mechanically caused bowel obstructions may occur as a result. Adhesions and the symptoms or follow-up operations resulting therefrom constitute a significant cost factor for the health sector. The laser is not very widespread as a hemostasis method since the method is very complicated and expensive from an apparatus point of view. Essentially, the same disadvantages occur as in electrosurgical hemostasis.

As stated above, thermal damage to the tissue situated around bleeding should always be expected during electrosurgical hemostasis. As a result of this, significant side effects can occur in thermally sensitive structures.

The most important disadvantage in all electrosurgical methods is the problem of optimum metering of the electrical energy. For a specific surgical intervention, the surgeon relies on general setting recommendations by the manufacturers. In this case, it is not possible to take into account the individual situation and the patient himself. What is more, many surgeons undertake subjective metering of the electrical energy, which can often not be justified by evidence-based discoveries and often leads to unnecessarily large thermal damages right up to very bad burns. The selection of the suitable parameters for a specific surgical application, such as current, current shape, voltage, power, pulsation etc., which ultimately characterize an electrosurgical mode, was often determined empirically by the system manufacturer and is often far removed from an optimum parameterization which is adapted to the respective situation and individual to the patient. Additionally, there is the incredibly large number of different modes which are available to the surgeon for his activity. By way of example, the ERBE VIO-system offers ten different modes for stopping bleeding. As a result of the large number of setting options, the surgeon is often unable to cope with searching for the optimum mode for the object to be achieved.

The group of so-called "non-thermal hemostasis" includes methods which undertake a biochemical intervention at bleeding sites. This includes the fibrin adhesive, which is a type of tissue adhesive and, as physiological two-component adhesive, adheres the edges of the wounds rather than closing them off by conventional sutures. An advantage of the fibrin adhesive is that it is gentle to particularly sensitive tissue. The initial substances—fibrin, thrombin, factor XIII and aprotinin—are biological substances, in which an infection by pathogens cannot be ruled out completely. The biological components are very expensive. Furthermore, collagen dressings can be used, particularly in the case of large-area bleeding. Collagen dressings are porous spongy wound dressings, which are obtained from a collagen dispersion by freeze-drying. They can take up the wound secretion and have a hemostatic effect. They promote the formation and organization of the body's own collagen. After contact with blood, the thrombocytes aggregate on the collagen fibers and cause the coagulation reaction. A disadvantage is that these dressings do not have the required efficiency in the case of acute bleeding and are more suitable for chronic bleeding.

In all of the above-described methods for stopping bleeding, anticoagulation means, hemodilution means such as Aspirin® or Marcumar® and the blood pressure considerably influence the efficiency of the hemostasis method. In the case of patients who have a coagulation disorder for hereditary reasons, for example bleeders or patients with hemophilia, the application of standard methods for stopping bleeding is often contraindicated.

Hemostasis after an injury occurs naturally by a sequence of complicated biochemical reactions, which reactions together are referred to as a coagulation cascade. The coagulation cascade consists of an intravascular and an extravascular system. Within the scope of the present invention, only the extravascular path is decisive, and so it should be discussed briefly in the following: the extravascular system is put into motion by an injury, which releases the tissue factor. The complex formed by tissue factor and factor VII puts into motion a cascade, which causes the activation of thrombin. Activated thrombin catalyses the reaction of fibrinogen into fibrin (final step of the coagulation cascade). Fibrin is initially present in the form of fibrin monomers, which finally cross-link to form a fibrin network. Hence this forms a fibrin clot, which stops the flow of blood.

The coagulation cascade explained above can be influenced by a so-called "dielectric barrier discharge". In this case, the four fibrinopeptides of the fibrinogen molecule are split and a fibrin monomer is created. This splitting process, which is catalyzed by thrombin in nature, forms the main precondition for the fibrin monomers to be cross-linked to form a fibrin clot. A dielectric barrier discharge is an electrical discharge between two electrodes which have a sufficiently high potential difference and are separated by an insulating dielectric barrier (insulator, dielectric). A weakly or non-conductive substance, whose charge carriers generally cannot move freely, is referred to as a dielectric. A dielectric can be a gas, a liquid or a solid. Insulators are referred to as dielectrics if magnetic or electric fields are applied to them. In contrast to a spark discharge, the dielectric prevents the development of a spark or an arc in the case of the dielectric barrier discharge and the discharge occurs either in the form of a so-called micro-discharge (FSD=filamentary silent discharge) or as a homogeneous discharge (GSD=glow silent discharge). These forms of discharge are very brief and have a low current and are therefore relatively silent. Since it is usually only electrons that are transferred during a silent discharge and the very energetic electrons can, as a result of the mass difference, only transfer relatively little energy onto the created ions in the case of the collision with gas atoms, the gas temperature is relatively low (cold plasma). In the case of dielectric barrier discharges, the distances between the electrode plates are usually 0.1 mm to a number of centimeters. In the surgical apparatus, the distance between the active electrode and the tissue is 0.1 mm to 1 cm. A high AC voltage in the radiofrequency or microwave frequency range, which usually lies in the region of 20 kV, is generally required for the dielectric barrier discharge. The generation of such a high voltage requires special generators with particularly tightly wound turns. This equipment is expensive and not used in electrosurgical systems. Incidentally, conventional electrosurgical systems supply voltages of at most 6 kV.

By way of example, a device for a dielectric barrier discharge is known from WO 2006/116252 A2. Therein, a silent discharge is carried out at relatively high voltages in the region of 20 kV. A corresponding device is also known from WO 2010/009103 A2. It claims a device for generating a dielectric barrier discharge for treatment of bleeding of the mucous membrane in the gastrointestinal tract. A portable device for generating plasma with relatively low temperature is claimed in US 2009/0206062 A1. The device serves for sterilization and blood coagulation. This therefore is hemostasis by thermal tissue coagulation, similar to argon plasma coagulation.

It is therefore an object of the present invention to stop, using a hemostasis instrument, the occurrence of bleeding, which may be caused by a surgical trauma, by the most minimally invasive means and, at the same time, with the greatest possible effectiveness and patient safety.

In order to achieve this object, a hemostasis instrument for actively stopping bleeding is proposed, which has the features of claim 1. It is used, in particular, after an open, laparoscopic or endoscopic operation on a patient and comprises a plurality of hemostasis components, wherein at least the following hemostasis components are provided in the hemostasis instrument:

- a thermal hemostasis apparatus for tissue coagulation for generating a temperature above the coagulation temperature of biological tissue by means of a coagulation electrode;
- a biochemical hemostasis apparatus for generating a dielectric barrier discharge by means of at least one discharge electrode and an insulation apparatus, wherein the insulation apparatus is arranged between the discharge electrode and the tissue to be treated;
- a supply apparatus for supplying substances influencing blood clotting to the tissue to be treated, and
- a supply apparatus for supplying noble gas to the tissue to be treated.

An essential feature of the invention therefore lies in the fact that a plurality of hemostasis components are unified in a single instrument such that bleeding can be stopped in a fashion adapted individually to the patient. As a result, bleeding can be stopped by particularly minimally invasive means, i.e. the treated tissue is coagulated as sparingly as possible. To this end, the hemostasis instrument according to the invention is provided with the option of stopping bleeding biochemically by means of a dielectric barrier discharge, also referred to as "silent discharge", and of stopping bleeding thermally by exogenous or endogenous heating of the biological tissue. Furthermore, the hemostasis instrument allows a supply of noble gas and substances influencing blood clotting to the tissue to be treated, such as, for example, the supply of fibrinogen, thrombin, aprotinin, blood clotting factors or other substances influencing blood clotting and therefore able to accelerate the hemostasis. As a result of this, bleeding can be stopped in a sparing manner by one and the same instrument, to be precise depending on the state of the individual patient. Depending on the type of bleeding to be stopped, it follows that use can be made of thermal hemostasis and/or biochemical hemostasis and substances influencing blood clotting can additionally be routed to the tissue to be treated. The supply of a noble gas firstly ensures that plasma coagulation can be carried out and secondly enables the generation of a dielectric barrier discharge using a conventional electrosurgical system with a voltage of at most 6 kV. The treated biological tissue does not heat up by any considerable amount in the case of a dielectric barrier discharge, and so the coagulation temperature (60° C.) of biological tissue is not reached, and it follows that there cannot be thermal damage to tissue by coagulation or even by carbonization or vaporization. In contrast to conventional hemostatic methods, the tissue is not heated during hemostasis by a dielectric barrier discharge, and so there is no denaturation of the proteins and the tissue remains biochemically intact. It follows that the present invention, by means of a single instrument, enables an optimum mixture of thermal and biochemical hemostasis, while possibly supplying required clot-promoting substances.

As stated above, the hemostasis instrument according to the invention enables the generation of a dielectric barrier discharge in a noble-gas atmosphere, for example by the use of argon, helium or neon, with the aid of which it becomes possible to keep the required voltages for generating a cold plasma (dielectric barrier discharge) below 4 kV. The dielectric barrier discharge can occur continuously or in a pulsing fashion. The hemostasis instrument offers both options. The insulation apparatus of the present invention can use a dielectric made of glass, more particularly made of quartz glass or any other suitable glass, ceramic, mica or similar materials.

A disadvantage of biochemical hemostasis methods is that the time until efficient hemostasis is reached is about 20 seconds. In order to be able to further shorten the time for blood clotting, the surgical apparatus according to the present invention offers the option of endogenous or exogenous heating of the blood to a temperature below the coagulation temperature of biological tissue, i.e. to a temperature below 60° C. To this end, the tissue can be preheated in a sparing fashion by conventional gas plasma by means of the hemostasis instrument according to the invention, without there being thermal damage to the tissue. Since the fibrinopeptides are stabilized by β-pleated sheets by means of hydrogen bonds, the supply of the above-described thermal energy leads to a breaking of these hydrogen bonds and hence to a destabilization of the fibrinopeptides. As a result, the fibrinopeptides can be split more easily by the application of the dielectric barrier discharge and there can be a faster onset of fibrin formation.

As stated previously, the hemostasis instrument according to the present invention has not only the option of biochemical hemostasis but, at the same time, also has the option of conventional thermal hemostasis by contact coagulation, argon plasma coagulation or by the option of a low-blood-loss radiofrequency incision. In thermal hemostasis, tissue temperatures above the coagulation temperature are reached, i.e. temperatures above 60° C., with the accompanying well-known tissue effects. As a result of applying supraphysiological temperatures above the coagulation temperature of the biological tissue, proteins and cell structures are changed, which can lead to cell death and subsequent tissue necrosis. A first step of these thermally induced changes lies in the denaturation of proteins and RNA, DNA and cell membrane components. If the tissue is continued to be heated above the coagulation temperature, tissue molecules are turned into smaller molecules, i.e. into decomposition products by splitting of covalent bonds. These molecules can furthermore react amongst themselves and new substances are created, which are cross-linked on the tissue surface. The overall process finally leads to bleeding being stopped.

In the case of patients with poor blood-clotting properties, the thermal and biochemical measures for stopping bleeding will not lead to the desired result. It is for this reason that the blood-clotting instrument according to the present invention comprises an integrated supply and metering system for fibrinogen, a fibrinogen preparation or another substance influencing the blood-clotting properties. This ensures that the formation of a fibrin network is promoted by the supply of an appropriate additive.

The hemostasis instrument according to the present invention preferably comprises a further hemostasis component in the form of a heating apparatus for endogenous or exogenous heating of the blood during a dielectric barrier discharge to a temperature below the coagulation temperature of biological tissue, i.e. below 60° C. Furthermore, the thermal hemostasis apparatus is preferably designed for contact coagulation or for plasma coagulation, in particular for argon plasma coagulation. A hemostasis instrument in which the coagulation electrode of the thermal hemostasis apparatus at the same time forms the discharge electrode of the biochemical hemostasis apparatus is particularly preferred. Here, the discharge electrode of the biochemical hemostasis apparatus can be designed as a ring electrode and arranged coaxially with respect to the coagulation electrode of the thermal hemostasis apparatus. Furthermore, the hemostasis instrument can comprise at least one tissue sensor which captures tissue effects generated during the use of one or more hemostasis components. By way of example, the tissue sensor can be integrated into the surgical instrument. However, it is also feasible for the tissue sensor to be integrated into the surgical equipment or for the at least one tissue sensor to be formed as an external separate unit. Furthermore, the hemostasis instrument can comprise at least one biosensor which captures patient information, for example by analyzing a bodily fluid of the patient, such that there is an optimum setting and/or combination of the individual hemostasis components, depending on situation- and patient-dependent influences. The at least one biosensor is preferably configured as vibration quartz sensor or as quartz crystal microbalance (QCM) sensor, which consists of a quartz disk with gold electrodes vapor deposited on both sides. A standing acoustic transverse wave is created within the quartz by applying an electrical AC voltage to the two gold electrodes. Here the vibration frequency depends on the mass accumulation on the upper electrode.

In order to achieve the aforementioned object, a surgical apparatus for stopping bleeding is also proposed, which has the features of claim 9. The surgical apparatus serves in particular for stopping bleeding after an open, laparoscopic or endoscopic operation on a patient and preferably comprises the following components:

at least one biosensor for capturing blood properties of a patient during, before or at the start of a surgical intervention;

a hemostasis instrument with a plurality of hemostasis components, wherein provision is made for at least one thermal hemostasis component and one biochemical hemostasis component, wherein there is an optimum setting and/or combination of the individual hemostasis components, respectively depending on the blood properties of the patient captured by the biosensor.

The surgical apparatus according to the present invention results in the advantage of bleeding being stopped by the use of a biosensor, respectively dependent on the patient's own blood properties and so hemostasis can occur in a more effective fashion. Otherwise, the advantages of the hemostasis instrument according to the present invention moreover emerge.

The thermal hemostasis component is preferably designed for tissue coagulation by generating a temperature above the coagulation temperature of biological tissue by means of a coagulation electrode, wherein the coagulation electrode is fed with RF-current. The thermal hemostasis component can furthermore be designed for contact coagulation or for plasma coagulation, in particular for argon plasma coagulation. By contrast, the biochemical hemostasis component is preferably designed to generate a dielectric barrier discharge by means of at least one discharge electrode and an insulation apparatus, wherein the insulation apparatus is arranged between the discharge electrode and the tissue to be treated and the discharge electrode is fed with RF-current. Moreover, provision is preferably made for a further hemostasis component in the form of a supply apparatus for supplying substances influencing blood clotting to the tissue to be treated. A further hemostasis component is preferably provided in the form of a supply apparatus for supplying noble gas, in particular argon, to the tissue to be treated. Moreover, provision can be made for a n even further hemostasis component in the form of a heating apparatus for endogenous or exogenous heating of the blood during a dielectric barrier discharge to a temperature below the coagulation temperature of biological tissue. Moreover, the surgical apparatus can comprise a tissue sensor which comprises tissue effects generated during the use of one or more hemostasis components and which is preferably arranged within the surgical instrument. An optimization of the setting and/or combination of the individual hemostasis components is preferably brought about on the basis of the captured values of the tissue sensor and of the biosensor in "real-time" by a control unit provided in the surgical apparatus.

The invention will be explained in more detail below on the basis of the drawing. In detail:

Figure 1C:
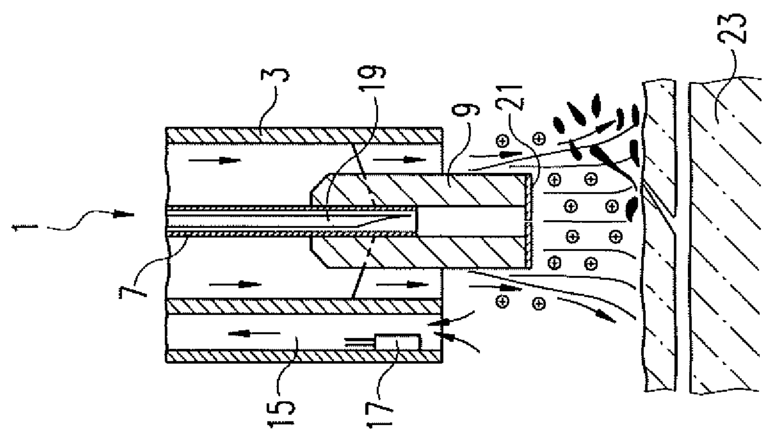
FIG. 1C shows a schematic illustration of the hemostasis instrument in accordance with FIG. 1A in a third operational state.
Figure 1B:
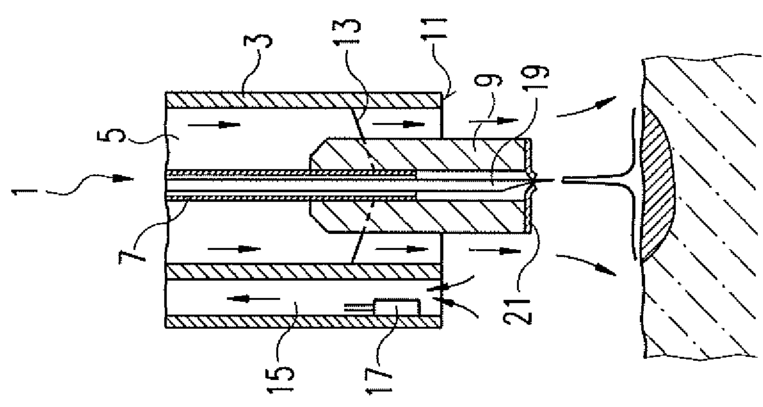
FIG. 1B shows a schematic illustration of the hemostasis instrument in accordance with FIG. 1A in a second operational state.
Figure 1A:
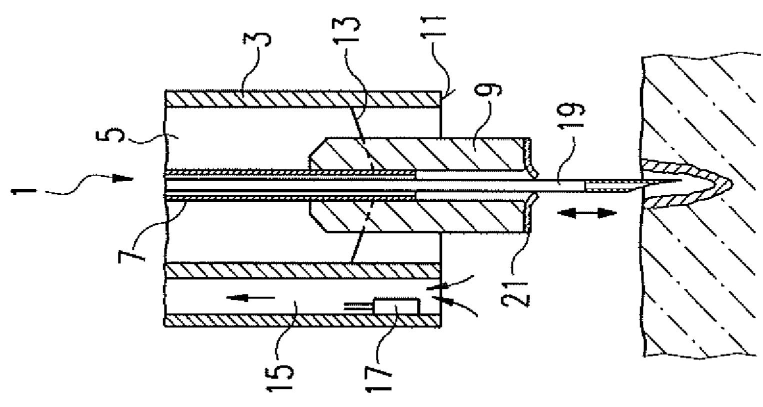
FIG. 1A shows a schematic illustration of a first embodiment of a hemostasis instrument for actively stopping bleeding, according to the present invention, in a first operational state.

FIG. 1A shows a schematic illustration of a first embodiment of the hemostasis instrument 1 for actively stopping bleeding, according to the present invention. The hemostasis instrument 1 comprises a duct or a tube 3, which encloses a lumen 5. Provided in the lumen is a supply and guidance channel 7, which projects into a distal end piece 9 of the hemostasis instrument 1, wherein the distal end piece 9 projects beyond the distal end 11 of the hemostasis instrument 1.

Both the supply and guidance channel 7 and also the distal end piece 9 are preferably arranged centrally in the lumen 5 of the tube 3. The distal end piece 9 is connected to the tube 3 by means of connection elements 13, which are only indicated here. A discharge channel 15 is provided parallel to the lumen 5 and adjoining the tube 3, with a tissue sensor 17 being provided at the distal end of said discharge channel, which tissue sensor is able to capture a tissue effect, for example smoke gas created during the operation. The emission gas is removed from the operation region by the discharge channel 15.

Provided in the supply and guidance channel 7 is an electrode 19, which is movably mounted in the supply and guidance channel 7 and can penetrate an insulation apparatus 21 situated at the distal end 21 of the distal end piece 9. To this end, the insulation apparatus 21 preferably has an elastic design and returns to its initial position as soon as the electrode 19 is arranged completely in the supply and guidance channel 7 (see FIG. 1C). So that the insulation apparatus 21 opens if the electrode 19 exerts a force thereon, it preferably has a slit or an opening of this type.

In the present exemplary embodiments, the electrode 19 is embodied as a hollow needle, by means of which a blood sample is obtained from the tissue to be treated, as illustrated in FIG. 1A. The hollow needle can also be used to carry out a radiofrequency incision in the tissue. The electrode 19 is connected to an RF-generator (not illustrated), which supplies a radiofrequency current to the electrode as soon as a radiofrequency incision, plasma coagulation or another electrosurgical application should be carried out in the tissue.

In FIG. 1B, the hemostasis instrument 1 is illustrated in a second operational state, in which the tip of the hollow needle, i.e. of the electrode 19, only projects minimally through the insulation apparatus 21 beyond the distal end of the distal end piece 9, while a radiofrequency current is supplied to the electrode 19. At the same time, an inert gas, in particular argon, is routed to the tissue via the lumen 5 or via the tube 3, as a result of which an argon plasma is created. Thus, provided the electrode 19 penetrates the insulation apparatus 21 and projects beyond the distal end of the distal end piece 9 in the direction of the tissue, a thermal hemostasis apparatus for tissue coagulation by generating a temperature above the coagulation temperature of biological tissue, i.e. above 60° C., is activated by means of the electrode 19, wherein the electrode acts as a coagulation electrode in this operational state. To the extent that the energy supplied to the electrode 19 is small, the thermal hemostasis apparatus can also serve to generate gas plasma which merely pre-heats the tissue in a sparing manner. It then forms a thermal heating apparatus at the same time.

FIG. 1C shows the hemostasis instrument 1 in a third operational state, in which the electrode 19 is completely arranged within the supply and guidance channel 7 and hence the insulation apparatus 21 completely closes off the distal outlet of the distal end piece 9 such that the electrode 19 is insulated with respect to the tissue 23. In this operational state of the hemostasis instrument 1, the insulation apparatus 21 is arranged between the (discharge) electrode 19 and the tissue to be treated. If an RF-current is supplied to the electrode 19 in this position, it acts as a discharge electrode for biochemical hemostasis for the purpose of generating a dielectric barrier discharge. Incidentally, the end piece 9 also preferably has an insulating design. It is also feasible for the end piece to be formed integrally with the insulation apparatus 21.

During the hemostasis by means of the dielectric barrier discharge shown in FIG. 1C, a fluid influencing blood clotting can be routed to the tissue via the lumen 5 or via the supply and guidance channel 7.

It follows that a biochemical hemostasis apparatus for generating a dielectric barrier discharge is realized in the position of the electrode 19 shown in FIG. 1C. Here, the insulation apparatus 21 serves as a dielectric in a noble-gas atmosphere, wherein the noble gas is in turn routed via the lumen 5 in the supply channel 3 to the tissue 23 in order to keep the voltage required for generating the dielectric barrier discharge below 4 kV.

Hence it is shown that the hemostasis instrument 1 according to the present embodiment has both a thermal hemostasis apparatus for tissue coagulation in the form of the movably mounted electrode 19 and, at the same time, a biochemical hemostasis apparatus for generating a dielectric barrier discharge by means of the discharge electrode 19, which in this case simultaneously forms the coagulation electrode, and an insulation apparatus 21, wherein the insulation apparatus is arranged between the discharge electrode, i.e. between the electrode 19 in this case, and the tissue 23 to be treated. Furthermore, provision is made for a supply apparatus in the form of the supply and guidance channel 7 and the lumen in the duct 3 which surrounds the distal end piece, for supplying noble gas and for supplying substances influencing blood clotting to the tissue to be treated. In the present exemplary embodiment, there is a "switch" between the two hemostasis apparatuses by displacing the electrode 19 from a first position within the supply and guidance channel 7 into a second position outside of the supply and guidance channel 7.

Figure 2C:
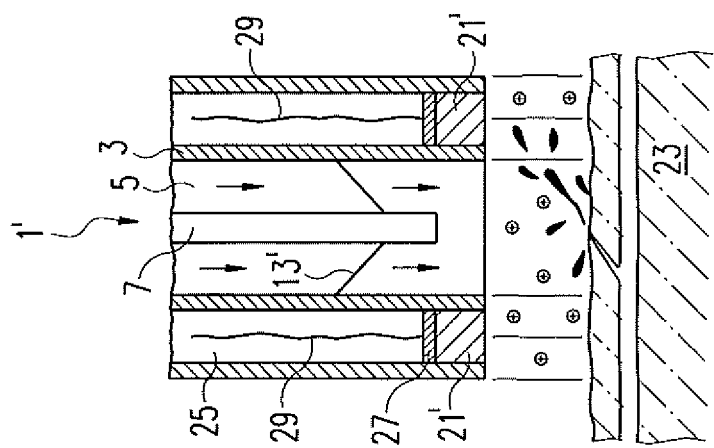
FIG. 2C shows a schematic illustration of the hemostasis instrument in accordance with FIG. 2A in a third operational state.
Figure 2B:
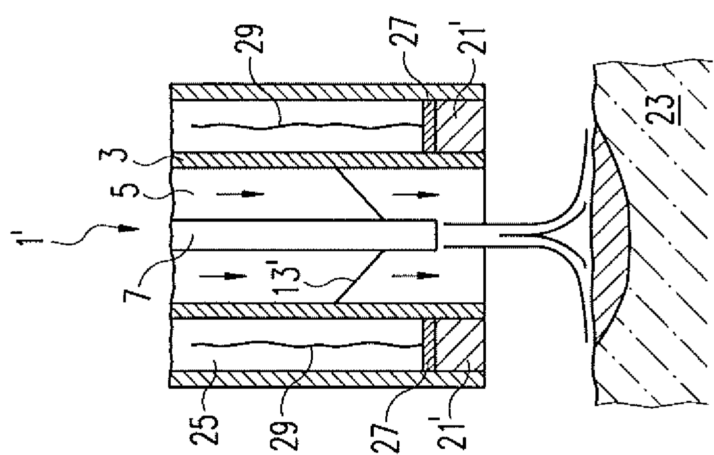
FIG. 2B shows a schematic illustration of the hemostasis instrument in accordance with FIG. 2A in a second operational state.
Figure 2A:
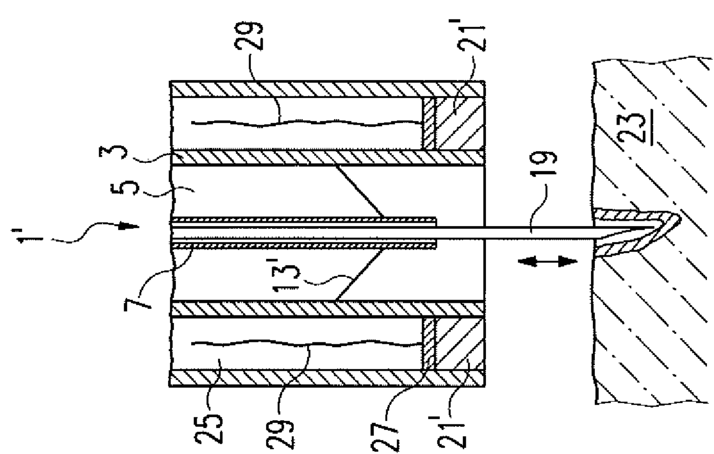
FIG. 2A shows a schematic illustration of a second embodiment of a hemostasis instrument according to the present invention in a first operational state.

A further embodiment of a hemostasis instrument is shown in FIGS. 2A to 2C. The hemostasis instrument 1' in accordance with FIGS. 2A to 2C differs from the hemostasis instrument 1 in accordance with FIGS. 1A to 1C by virtue of the fact that, in particular, no distal end piece is provided in the hemostasis instrument 1', but rather that the supply and guidance channel 7 with the electrode 19 mounted therein is attached to the tube 3 by means of connection elements 13', wherein said electrode in turn is embodied as a hollow needle, in particular for taking a blood sample. In this embodiment of the invention, the electrode 19 is simultaneously also embodied as a hollow needle and movably mounted in the guidance channel 7.

Moreover, the hemostasis instrument 1' in accordance with FIGS. 2A to 2C differs from the embodiment in FIGS. 1A to 1C by virtue of the fact that the insulation apparatus 21' is embodied as an annular body, which is arranged at the distal end of an annular space or channel 25 surrounding the lumen 5 or the duct 3 in a coaxial fashion. An annular discharge electrode 27 is provided at the proximal end of the insulation apparatus 21', which discharge electrode rests in planar fashion against the insulation apparatus 21 and, as a result, likewise surrounds the tube 3 in the channel 25 in a coaxial fashion. The discharge electrode 27 is connected to a corresponding voltage or current source, in particular to the RF-generator of an item of surgical equipment by means of feed lines 29.

Overall, it was shown that in the present embodiment, the coagulation electrode, i.e. the electrode 19, and the discharge electrode 27 of the biochemical hemostasis apparatus are embodied as separate elements.

FIG. 2B shows the hemostasis instrument 1' in an operational state, in which the thermal hemostasis apparatus for tissue coagulation can occur by generating a temperature above the coagulation temperature of biological tissue by means of the coagulation electrode 19. In this case, the hollow needle acting as electrode 19 has in turn been withdrawn into the feed and guiding channel 7 while a radiofrequency current is applied to the electrode 19 (not visible in FIG. 2B). At the same time, an inert gas, in particular argon, is routed through the lumen 5 to the tissue 23 to be treated, and so an argon plasma is created between the hemostasis instrument 1' and the tissue 23.

FIG. 2C shows the hemostasis instrument 1 in accordance with the present embodiment in an activated operational state of the biochemical hemostasis apparatus. In this operational state, an inert gas, in particular a noble gas in the form of argon, is in turn guided to the tissue 23 through the lumen 5, while an RF-current is at the same time applied to the discharge electrode 27 via the feed line 29 such that a dielectric barrier discharge, i.e. a cold plasma, forms between the discharge electrode 27 and the tissue 23 acting as second electrode. At the same time, a supply apparatus for supplying substances influencing blood clotting to the tissue to be treated can be formed by the lumen 5 of the tube 3.

The hemostasis instrument 1' in accordance with FIGS. 2A to 2C enables radiofrequency incisions of biological tissue using a centrally arranged extendable RF-electrode 19, which more particularly has the shape of a hollow needle. Overall, the hemostasis instrument 1' can realize both thermal hemostasis by means of the coagulation electrode 19 and biochemical hemostasis by means of the discharge electrode 27. The hemostasis instrument 1' according to the present invention is moreover suitable for supplying liquids such as e.g. adducts, which should support the non-thermal, i.e. the biochemical, hemostasis, in particular for supplying fibrinogen, thrombin, blood clotting factors or the like. Moreover, the instrument for supplying a fluid is suitable for clearing the operation site after bleeding by rinsing.

Figure 3C:
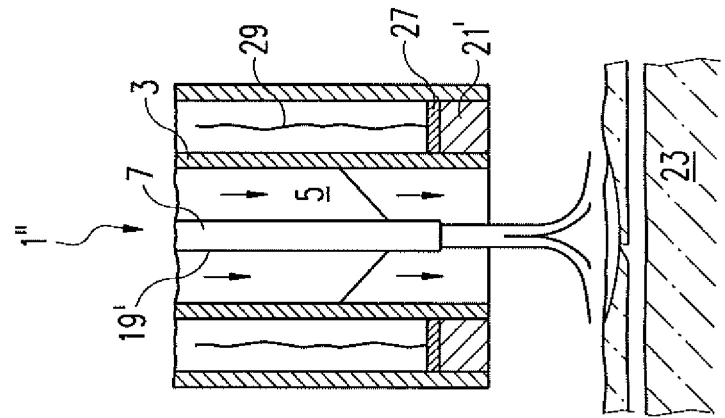
FIG. 3C shows a schematic illustration of the hemostasis instrument in accordance with FIG. 3A in a third operational state.
Figure 3B:
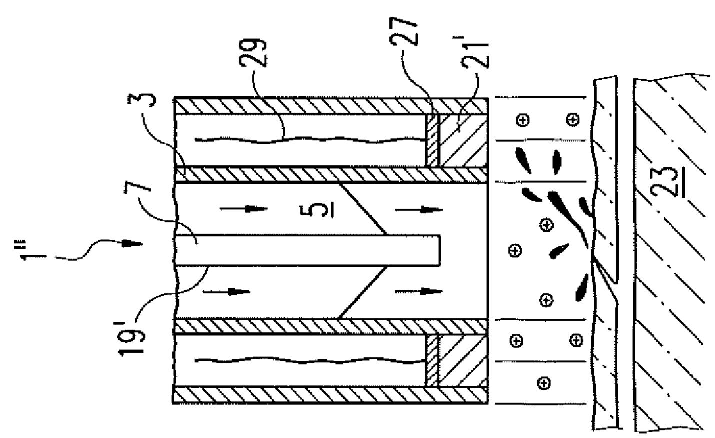
FIG. 3B shows the hemostasis instrument in accordance with FIG. 3A in a second operational state.
Figure 3A:
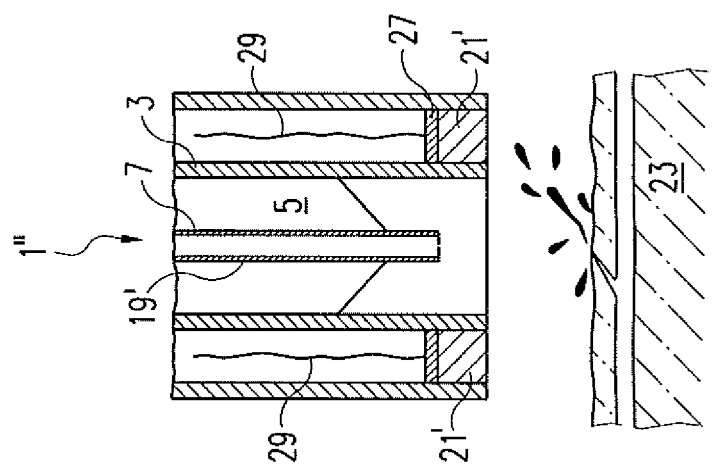
FIG. 3A shows a schematic illustration of a further embodiment of the hemostasis instrument according to the present invention in a first operational state.

FIGS. 3A to 3C show a further embodiment of a hemostasis instrument according to the invention. In contrast to the hemostasis instrument 1' in accordance with FIGS. 2A to 2C, the supply and guidance channel 7 in the present case is embodied as electrode 19', i.e. it does not comprise a hollow needle mounted therein. In this embodiment, the supply and guidance channel 7 can simultaneously serve as a supply line for a liquid, in particular by generating a conical beam, by means of which, in particular, the supply of substances influencing blood clotting to the tissue 23 to be treated is ensured. Otherwise, the embodiment and the functionality thereof correspond to the embodiment according to FIGS. 2A to 2C, to which reference is made herewith.

It is also possible to identify in FIG. 3B, that the supply apparatus for supplying substances influencing blood clotting to the tissue 23 to be treated via the supply channel 7 can be activated during a dielectric barrier discharge, i.e. in the case of an active biochemical hemostasis apparatus. A noble gas can once again be supplied via the lumen 5. It is understood that the supply apparatus for supplying substances influencing blood clotting can also be active independently of the respective hemostasis mode.

Figure 4:
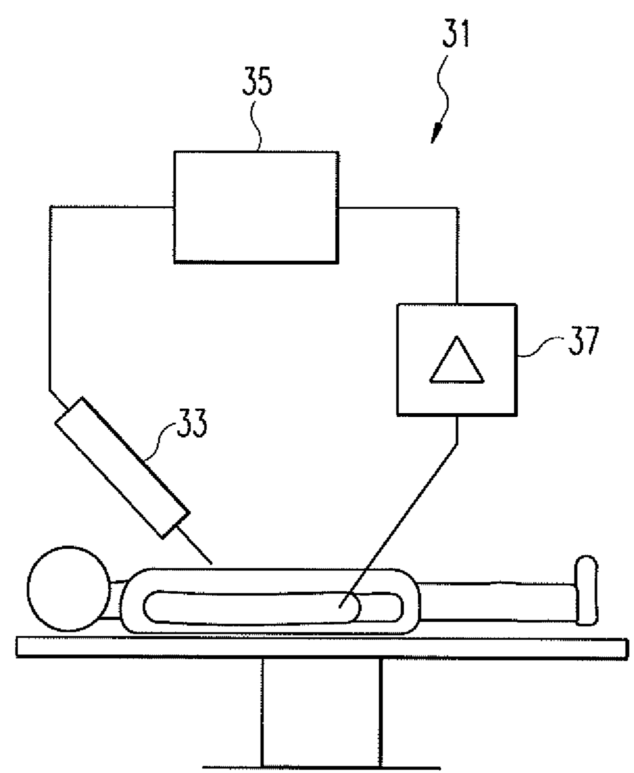
FIG. 4 shows a schematic illustration of a surgical apparatus according to the present invention.

FIG. 4 still shows a schematic illustration of a surgical apparatus 31 according to the present invention. The surgical apparatus 31 comprises a surgical instrument, more particularly an electrosurgical instrument 33, a control apparatus 35 and a biosensor 37. The biosensor 37 is designed to capture the blood properties of a patient during, before or at the start of a surgical intervention. To this end, the biosensor preferably comprises a piezoelectric element or the like, in order to determine what blood-clotting properties a patient has. The captured data from the biosensor can then be transmitted to a control unit 35, which undertakes the appropriate setting of the RF-generator or other surgical aids for carrying out the surgical intervention.

The captured data from the biosensor are preferably used to undertake an appropriate setting and, in particular, an appropriate combination of the thermal hemostasis component and the biochemical hemostasis component and the other hemostasis components. By way of example, the blood picture or the blood-clotting properties of the patient can be analyzed by means of the biosensor. By way of example, use can be made of a "quartz crystal microbalance" sensor (Gehring et al.) in order to establish the prothrombin time (PT time), which allows a statement to be made about the patient's individual blood-clotting properties. As a result of this, an optimum setting of the surgical apparatus from biochemical and thermal hemostasis and the supply of adducts, i.e. means influencing blood clotting, and the supply of a noble gas can be established and provided by the surgical apparatus. This means that the individual components can be applied successively or simultaneously with different weightings depending on the clotting signal of the biosensor, wherein it is not mandatory for every component to be used in every surgical intervention.

An actually generated tissue effect during an operation is detected by means of the tissue sensor 17. By way of example this can occur via the qualitative or quantitative capture of the smoke gas created during the application or by the detection of the electromagnetic radiation of an application of a medical plasma application. There can be a real-time optimization of the surgical application from the biochemical sensor signal and the tissue-effect signal by the control unit. Finally, this provides a patient specific option to stop bleeding with minimal damage to the surrounding tissue.

LIST OF REFERENCE SIGNS

1 Hemostasis instrument
1' Hemostasis instrument
1" Hemostasis instrument
3 Tube
5 Lumen
7 Supply and guidance channel
9 Distal end piece
11 Distal end
13 Connection element
13' Connection element
15 Discharge channel
17 Tissue sensor
19 Electrode
19' Electrode
21 Insulation apparatus
21' Insulation apparatus
23 Tissue
25 Channel
27 Discharge electrode
29 Feed line
31 Surgical apparatus
33 Surgical instrument
35 Control unit
37 Biosensor

The invention claimed is:

1. A hemostasis instrument for actively stopping bleeding comprising a plurality of hemostasis components, wherein at least the following hemostasis components are provided:

a thermal hemostasis apparatus for tissue coagulation by generating a temperature above the coagulation temperature of biological tissue by a coagulation electrode, the thermal hemostasis apparatus including a lumen and a channel extending within the lumen and beyond a terminal face of the lumen, wherein the coagulation electrode is axially movable within the channel;

a biochemical hemostasis apparatus for generating a dielectric barrier discharge which does not heat the biological tissue by an amount sufficient to raise the temperature of the biological tissue to the coagulation temperature of the biological tissue; the biochemical hemostasis apparatus comprising at least one discharge electrode and an elastic insulation apparatus, wherein the elastic insulation apparatus is disposed at a distal end of the channel in spaced relation with a distal end of the lumen and the elastic insulation apparatus is adapted to be arranged between the at least one discharge electrode and a tissue to be treated, and wherein the coagulation electrode of the thermal hemostasis apparatus at the same time forms the discharge electrode of the biochemical hemostasis apparatus and the at least one discharge electrode is capable of penetrating through the elastic insulation apparatus;

a supply apparatus for supplying substances influencing blood clotting to the tissue to be treated, and a supply apparatus for supplying noble gas to the tissue to be treated.

2. The hemostasis instrument of claim 1, wherein the hemostasis instrument comprises a further hemostasis component in a form of a thermal hemostasis apparatus for endogenous or exogenous heating of the blood during a dielectric barrier discharge to a temperature below a coagulation temperature of biological tissue.

3. The hemostasis instrument of claim 1, wherein the thermal hemostasis apparatus is designed for contact coagulation or for plasma coagulation.

4. The hemostasis instrument of claim 1, wherein the hemostasis instrument comprises at least one tissue sensor which is adapted to capture tissue effects generated during use of one or more hemostasis components.

5. The hemostasis instrument of claim 1, wherein an optimum setting of the hemostasis instrument depends on situation- and patient-dependent influences.

6. The hemostasis instrument of claim 5, wherein the patient-dependent influences are available in the form of patient information captured by at least one biosensor.

7. A surgical apparatus for stopping bleeding comprising:

at least one biosensor for capturing blood properties of a patient during, before, or at the start of a surgical intervention;

a hemostasis instrument with a plurality of hemostasis components comprising at least one thermal hemostasis component and one biochemical hemostasis component, the thermal hemostasis component including a lumen and a channel extending within the lumen and beyond a terminal face of the lumen, the biochemical hemostasis component comprising at least one discharge electrode and an insulation apparatus, wherein the insulation apparatus is disposed at a distal end of the channel in spaced relation with a distal end of the lumen and the elastic insulation apparatus is adapted to be arranged between the discharge electrode and the tissue to be treated and the discharge electrode is fed with RF-current, wherein a coagulation electrode of the thermal hemostasis apparatus at the same time forms the discharge electrode of the biochemical hemostasis apparatus, and wherein the coagulation electrode is axially movable within the channel, wherein the at least one discharge electrode is capable of penetrating through the insulation apparatus, and wherein an optimum setting of the hemostasis instrument depends on the blood properties of the patient captured by the at least one biosensor, wherein the biochemical hemostasis component is designed to generate a dielectric barrier discharge which does not heat the tissue by an amount sufficient to raise the temperature of the biological tissue to the coagulation temperature of the biological tissue.

8. The surgical apparatus of claim 7, wherein the thermal hemostasis component is designed for tissue coagulation by generating a temperature above the coagulation temperature of biological tissue by a coagulation electrode, which is fed with RF-current.

9. The surgical apparatus of claim 8, wherein the thermal hemostasis component is designed for contact coagulation or for plasma coagulation.

10. The surgical apparatus of claim 7, further comprising a hemostasis component in a form of a supply apparatus for supplying substances influencing blood clotting to a tissue to be treated.

11. The surgical apparatus of claim 7, further comprising a hemostasis component in a form of a supply apparatus for supplying noble gas to a tissue to be treated.

12. The surgical apparatus of claim 7, further comprising a hemostasis component in a form of a thermal hemostasis apparatus for endogenous or exogenous heating of the blood during a dielectric barrier discharge to a temperature below a coagulation temperature of biological tissue.

13. The surgical apparatus of claim 7, wherein the surgical apparatus comprises a tissue sensor which is adapted to capture tissue effects generated during the use of one or more hemostasis components.

14. The surgical apparatus of claim 12, wherein the surgical apparatus is configured in such a way that the setting of the hemostasis instrument can be optimized based on captured values of a tissue sensor and of the biosensor in "real-time" by a control unit provided in the surgical apparatus.

15. The hemostasis instrument of claim 1, wherein the substances influencing blood clotting comprise fibrinogen, thrombin, aprotinin, blood clotting factors or a combination thereof.

16. The surgical apparatus of claim 10, wherein the substances influencing blood clotting comprise fibrinogen, thrombin, aprotinin, blood clotting factors, or a combination thereof.

17. The hemostasis instrument of claim 3, wherein the plasma coagulation is argon plasma coagulation.

18. A hemostasis instrument for actively stopping bleeding comprising a plurality of hemostasis components, wherein at least the following hemostasis components are provided:

a thermal hemostasis apparatus for tissue coagulation by generating a temperature above the coagulation temperature of biological tissue by a coagulation electrode, the thermal hemostasis apparatus including a lumen and a channel extending within the lumen and beyond a terminal face of the lumen, wherein the coagulation electrode is axially movable within the channel;

a biochemical hemostasis apparatus for generating a dielectric barrier discharge which does not heat the biological tissue by an amount sufficient to raise the temperature of the biological tissue to the coagulation temperature of the biological tissue; the biochemical hemostasis apparatus comprising at least one discharge electrode and an insulation apparatus, wherein the insulation apparatus is disposed at a distal end of the channel in spaced relation with a distal end of the lumen and the elastic insulation apparatus is adapted to be arranged between the at least one discharge electrode and a tissue to be treated, and wherein the coagulation electrode of the thermal hemostasis apparatus at the same time forms the discharge electrode of the biochemical hemostasis apparatus and the at least one discharge electrode is capable of penetrating through the insulation apparatus;

a supply apparatus for supplying substances influencing blood clotting to the tissue to be treated; and a supply apparatus for supplying noble gas to the tissue to be treated;

wherein the thermal hemostasis apparatus is designed for contact coagulation.

19. The hemostasis instrument of claim 18, wherein the hemostasis instrument comprises a further hemostasis component in a form of a thermal hemostasis apparatus for endogenous or exogenous heating of the blood during a dielectric barrier discharge to a temperature below a coagulation temperature of biological tissue.

20. The hemostasis instrument of claim 18, wherein the hemostasis instrument comprises at least one tissue sensor which is adapted to capture tissue effects generated during use of one or more hemostasis components.

* * * * *